(12) United States Patent
Yuan et al.

(10) Patent No.: US 12,429,470 B2
(45) Date of Patent: Sep. 30, 2025

(54) ULTRAFAST RESPONSE HYDROGEN SENSOR

(71) Applicant: University of Electronic Science and Technology of China, Sichuan (CN)

(72) Inventors: Zhen Yuan, Sichuan (CN); Huiling Tai, Sichuan (CN); Yadong Jiang, Sichuan (CN); Ruilin Yang, Sichuan (CN); Tiancheng Huang, Sichuan (CN); Chen Shan, Sichuan (CN)

(73) Assignee: University of Electronic Science and Technology of China, Sichuan (CN)

( * ) Notice: Subject to any disclaimer, the term of this patent is extended or adjusted under 35 U.S.C. 154(b) by 0 days.

(21) Appl. No.: 18/969,096

(22) Filed: Dec. 4, 2024

(65) Prior Publication Data

US 2025/0102484 A1  Mar. 27, 2025

(30) Foreign Application Priority Data

Apr. 23, 2024  (CN) .......................... 202410489655.3

(51) Int. Cl.
*G01N 33/00* (2006.01)

(52) U.S. Cl.
CPC ....... *G01N 33/0031* (2013.01); *G01N 33/005* (2013.01)

(58) Field of Classification Search
CPC .......................... G01N 33/005; G01N 33/0031
See application file for complete search history.

(56) References Cited

U.S. PATENT DOCUMENTS

2023/0059356 A1* 2/2023 Meinhold ............... G01M 3/20

FOREIGN PATENT DOCUMENTS

| | | | | |
|---|---|---|---|---|
| CN | 117288807 | A | * 12/2023 | |
| CN | 117388330 | A | * 1/2024 | ............ G01N 27/12 |
| JP | 201675597 | A | 5/2016 | |
| JP | 5936087 | B2 | * 6/2016 | |
| TW | 1457560 | | * 10/2014 | |

OTHER PUBLICATIONS

Machine Translation of CN 117288807 (Year: 2023).*
Machine Translation of CN 117388330 (Year: 2024).*
Machine Translation of JP 5936087 (Year: 2016).*
Machine Translation of TW 1457560 (Year: 2014).*

* cited by examiner

*Primary Examiner* — Nathaniel J Kolb

(57) ABSTRACT

An integrated structure of an ultrafast response hydrogen sensor includes: a gas path chamber; a gas extractor fixed to a gas inlet of the gas path chamber; and a first hydrogen sensor and a second hydrogen sensor provided inside the gas path chamber; wherein the gas extractor is located in an identical straight line with the first hydrogen sensor and the second hydrogen sensor; the first hydrogen sensor and the second hydrogen sensor each have an Port A and a Port B, and DC voltage is applied to the Port A of the first hydrogen sensor and the Port B of the second hydrogen sensor, and the Port B of the first hydrogen sensor is connected to the Port A of the second hydrogen sensor to form a shared port, and the shared port serves as a voltage output port.

6 Claims, 7 Drawing Sheets

ULTRAFAST RESPONSE HYDROGEN SENSOR

CROSS REFERENCE OF RELATED APPLICATION

The present application claims priority under 35 U.S.C. 119(a-d) to CN2024104896553, filed Apr. 23, 2024.

BACKGROUND OF THE PRESENT INVENTION

Field of Invention

The present invention belongs to the technical field of gas sensors, and more particular to an integrated structure of an ultrafast response hydrogen sensor.

Description of Related Arts

In recent years, with the rapid development of the hydrogen energy industry, safety issues have received more and more attention. Hydrogen is a colorless and odorless gas with a large explosive concentration range which is at a range of 4-75 vol %, and there is an urgent need to monitor the concentration of the hydrogen in real time. For hydrogen detection in automobiles and fixed power systems, relevant departments have stipulated that the response time and recovery time of hydrogen sensors are expected to be within 1 second.

Semiconductor metal oxide hydrogen sensors made of have the advantages of simple structure, low price, high sensitivity, and batch manufacturing. Through research, the hydrogen sensors are expected to overcome the shortcomings of traditional hydrogen sensors and be widely used in the field of new energy vehicles. However, semiconductor metal oxide hydrogen sensors still cannot meet the application requirements of hydrogen leakage detection in terms of response speed. It is a method worth exploring to optimize the sensor structure and circuit algorithm design to achieve rapid detection of hydrogen leakage. For example, a Chinese patent with application No. 202211628182.8 discloses a method for rapid prediction of hydrogen concentration based on CNN-LSTM (convolutional neural network-long short-term memory network). This method calculates and achieves hydrogen concentration prediction by extracting the initial response stage of the first 30 s of the hydrogen sensor response-recovery curve. However, the method takes a long time to predict the hydrogen concentration, which does not meet the satisfying response speed requirements. Therefore, it is necessary to seek a rapid hydrogen detection method with a faster response speed.

SUMMARY OF THE PRESENT INVENTION

In view of the problem that conventional hydrogen sensors have a long response time, the present invention provides an ultrafast response hydrogen sensor integrated structure, which achieves rapid detection of hydrogen concentration by collecting voltage differential signals between two hydrogen sensors, and has a wide range of applications in the fields of new energy gas, hydrogen energy battery, etc.

In order to achieve the above objects, technical solutions adopted by the present invention are as follows:

An integrated structure of an ultrafast response hydrogen sensor comprises: a gas path chamber; a gas extractor fixed to a gas inlet of the gas path chamber; and a first hydrogen sensor and a second hydrogen sensor provided inside the gas path chamber;

wherein the gas extractor is located in an identical straight line with the first hydrogen sensor and the second hydrogen sensor; the first hydrogen sensor and the second hydrogen sensor each have an Port A and a Port B, and DC voltage is applied to the Port A of the first hydrogen sensor and the Port B of the second hydrogen sensor, and the Port B of the first hydrogen sensor is connected to the Port A of the second hydrogen sensor to form a shared port, and the shared port serves as a voltage output port.

Preferably, a distance between the first hydrogen sensor and the second hydrogen sensor is at a range of 1 mm to 35 cm.

Preferably, a gas flow rate generated by the gas extractor is at a range of 5-500 sccm.

Preferably, the first hydrogen sensor and the second hydrogen sensor have identical structure and hydrogen-sensitive characteristics.

Preferably, a hydrogen-sensitive material of the first hydrogen sensor and the second hydrogen sensor is specifically a palladium metal material, or a composite material consisting of a palladium metal material and at least one metal material, wherein the metal material is nickel, gold, ruthenium, cobalt or titanium.

Preferably, the composite material is a layered stacked material or an alloy material.

Preferably, a distance between the first hydrogen sensor and the second hydrogen sensor, and a gas flow rate generated by the gas extractor are adjusted to control a response time and a response rate of the ultrafast response hydrogen sensor of the integrated structure.

Taking the integrated structure of the ultrafast response hydrogen sensor in which the first hydrogen sensor is located between the gas extractor and the second hydrogen sensor as an example, its working principle is as follows.

When the integrated structure of the ultrafast response hydrogen sensor starts to detect hydrogen in an initial state, the hydrogen flows through the gas path chamber driven by the gas extractor. When the hydrogen flows through the first hydrogen sensor, a resistance value of the first hydrogen sensor begins to increase, and a voltage of the voltage output port begins to increase; when the hydrogen flows through the second hydrogen sensor, the resistance value of the second hydrogen sensor begins to increase, and the voltage of the voltage output port begins to decrease and gradually stabilizes; during the hydrogen detection period, the resistance differential signal between the first hydrogen sensor and the second hydrogen sensor is converted into a voltage differential signal. By detecting the time from the initial state to the peak of the voltage differential signal, response time and response rate of the integrated structure of the ultrafast response hydrogen sensor are determined; further, by detecting the peak value of the voltage differential signal, the hydrogen concentration is characterized.

After the hydrogen detection is completed, when the air flows the gas path chamber through the gas extractor and flows through the first hydrogen sensor, the resistance value of the first hydrogen sensor decreases, and the voltage of the voltage output port begins to decrease; when the air flows through the second hydrogen sensor, the resistance value of the second hydrogen sensor decreases, and the voltage of the voltage output port begins to increase and gradually stabilizes. At this time, the integrated structure of the ultrafast response hydrogen sensor recovers to the initial state, and the next hydrogen detection can be performed.

Compared with the conventional arts, the beneficial effects of the present invention are as follows.

1. The present invention provides the integrated structure of the ultrafast response hydrogen sensor, which utilizes the time difference of the hydrogen reaching two hydrogen sensors and combines circuit design to collect the voltage differential signal of the two hydrogen sensors to achieve rapid response of hydrogen and rapid detection of concentration; compared with the concentration signal reading of the traditional resistive gas sensor, which requires a stable response, the detection time of the present invention is shorter, which greatly improves the hydrogen response speed;
2. Preferably, the present invention can control the hydrogen response time and response rate by adjusting the distance between the two hydrogen sensors and the gas flow rate generated by the gas extractor, which can be applied to different scenarios of hydrogen detection requirements and has a wide range of application backgrounds in the fields of new energy gas, hydrogen energy battery, etc.

BRIEF DESCRIPTION OF THE DRAWINGS

In order to more clearly illustrate the technical solutions in the embodiments of the present invention or the conventional arts, the drawings required for utilizing in the description of the embodiments or the conventional arts will be briefly introduced below. Apparently, the drawings described below are only some embodiments of the present invention. For one skilled in the art, other drawings can be obtained based on these drawings without creative work.

The descriptions of the marks in the accompanying drawings are as follows:

101—first hydrogen sensor; 102—second hydrogen sensor; 2—gas path chamber; 3—gas extractor; 4—voltage output port; 5—voltage source; 6—ground terminal.

DETAILED DESCRIPTION OF THE PREFERRED EMBODIMENT

In order to further understand the present invention, the preferred embodiments of the present invention are described below in conjunction with the examples, but it should be understood that these descriptions are only for further illustrating the features and advantages of the present invention, rather than limiting the claims of the invention. All raw materials of the present invention are not particularly limited in their sources, and can be purchased on the market or prepared according to conventional methods well known to those skilled in the arts.

Embodiment 1

Figure 1:
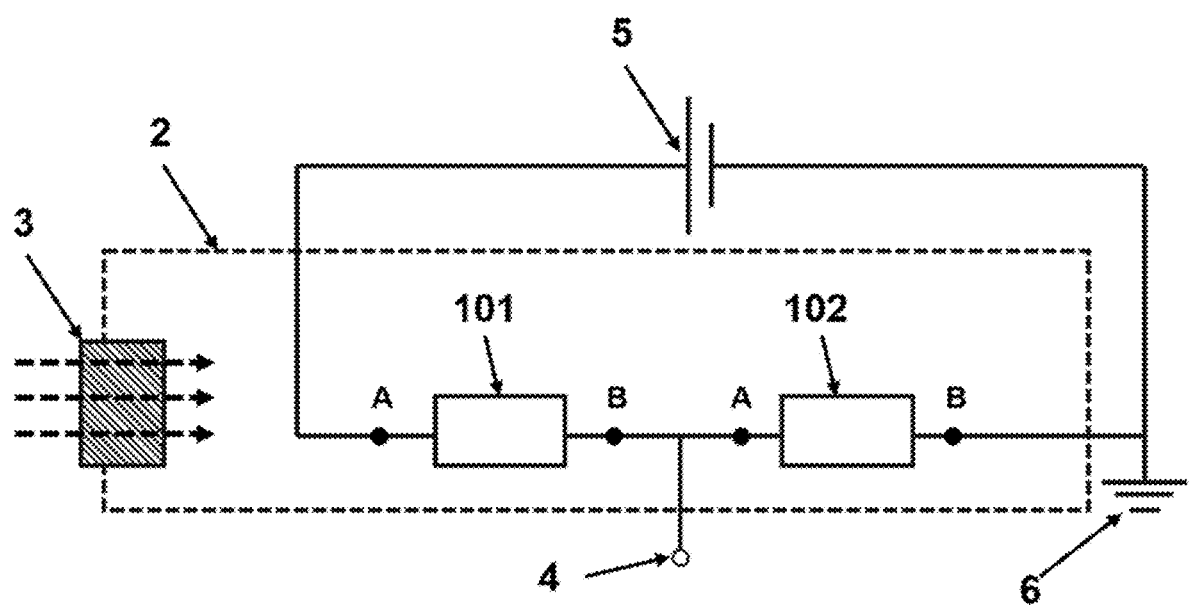
FIG. 1 is a schematic diagram of an integrated structure of an ultrafast response hydrogen sensor according to an Embodiment 1 of the present invention.

Referring to FIG. 1, this embodiment provides an integrated structure of an ultrafast response hydrogen sensor comprising: a gas path chamber 2; a gas extractor 3 fixed to a gas inlet of the gas path chamber 2; and a first hydrogen sensor 101 and a second hydrogen sensor 102 provided inside the gas path chamber 2;

The gas extractor 3 is located in an identical straight line with the first hydrogen sensor 101 and the second hydrogen sensor 102 in sequence; the first hydrogen sensor 101 and the second hydrogen sensor 102 each have an Port A and a Port B, and DC voltage is applied to the Port A of the first hydrogen sensor 101 and the Port B of the second hydrogen sensor 102, that is, a voltage source 5 is provided between the Port A of the first hydrogen sensor 101 and the Port B of the second hydrogen sensor 102, and the Port B of the first hydrogen sensor 101 is connected to the Port A of the second hydrogen sensor 102 to form a shared port, and the shared port serves as a voltage output port 4 of the ultrafast response hydrogen sensor integrated structure; a ground port 6 is provided between the Port B of the second hydrogen sensor 102 and the voltage source 5.

In this embodiment, the first hydrogen sensor 101 and the second hydrogen sensor 102 have identical structure and hydrogen-sensitive characteristics, and both utilize a layered palladium-nickel nanofilm with a thickness of 16 nm as a hydrogen-sensitive material; a distance between the first hydrogen sensor 101 and the second hydrogen sensor 102 is 25 cm; a gas flow rate generated by the gas extractor 3 is 300 sccm; the voltage source 5 provides a voltage of 5 V; and a sampling frequency of the voltage output port 4 is 100 Hz.

Figure 2:
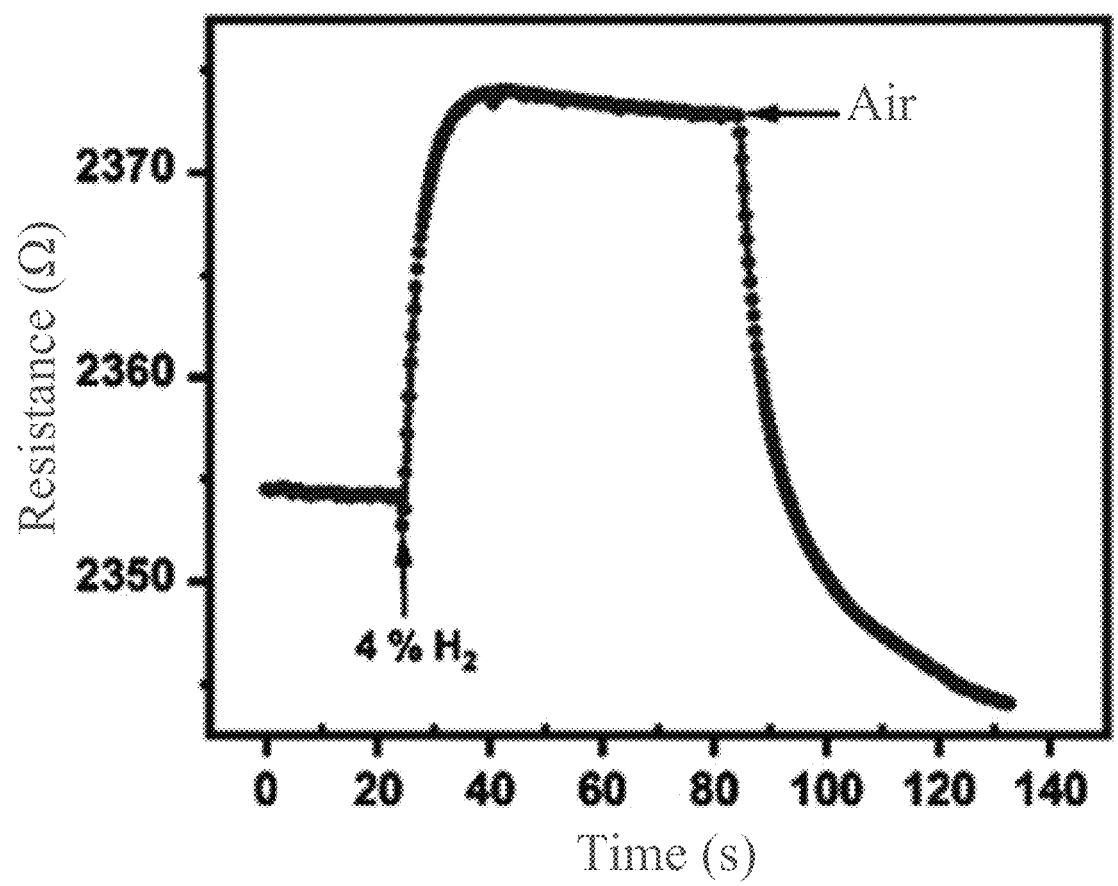
FIG. 2 is a resistance signal curve of hydrogen response of the first hydrogen sensor according to the Embodiment 1 of the present invention.
Figure 3:
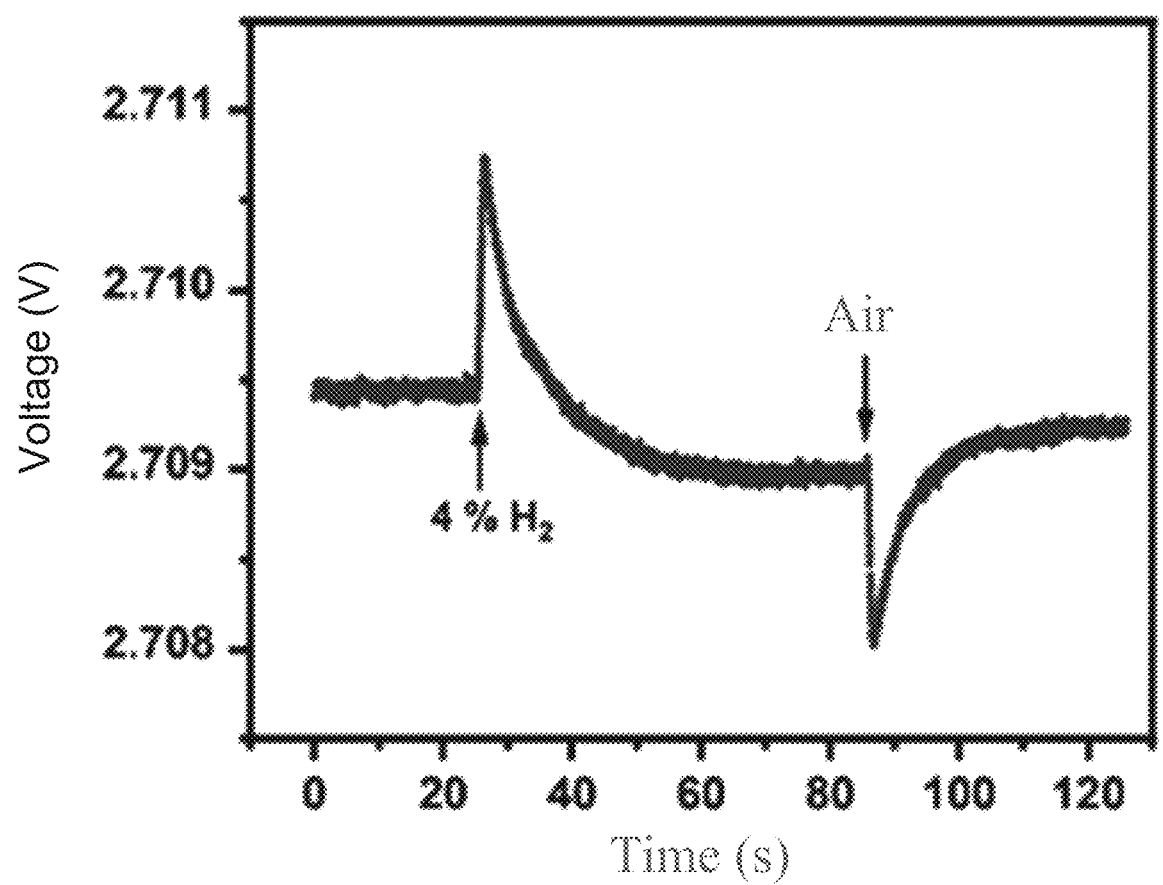
FIG. 3 is a hydrogen response voltage differential signal output curve outputted by the voltage output port according to the Embodiment 1 of the present invention.

The performance test on the integrated structure of the ultrafast response hydrogen sensor provided in this embodiment was carried out, specifically detecting hydrogen with a concentration of 4%. During this period, a resistance signal curve of hydrogen response of the first hydrogen sensor 101 is shown in FIG. 2, and a hydrogen response voltage differential signal output curve outputted by the voltage output port 4 is shown as in FIG. 3. The detection process is as follows:

At about 25th second, the integrated structure of the ultrafast response hydrogen sensor in an initial state starts to detect hydrogen, and the hydrogen flows the gas path chamber 2 through the gas extractor 3. When the hydrogen flows through the first hydrogen sensor 101, a resistance value of the first hydrogen sensor 101 begins to increase, and a voltage of the voltage output port 4 begins to increase; when the hydrogen flows through the second hydrogen sensor 102, the resistance value of the second hydrogen sensor 102 begins to increase, and the voltage of the voltage output port 4 begins to decrease and gradually stabilizes; during the hydrogen detection period, the resistance differential signal between the first hydrogen sensor 101 and the second hydrogen sensor 102 is converted into a voltage differential signal as shown in FIG. 3. By detecting the time from response to peak of the voltage differential signal, response time and response rate of the integrated structure of the ultrafast response hydrogen sensor are determined; further, by detecting the peak value of the voltage differential signal, the hydrogen concentration is characterized.

After the hydrogen detection is completed, the integrated structure of the ultrafast response hydrogen sensor is recovered at about 85th seconds. When the air flows the gas path chamber 2 through the gas extractor 3 and flows through the first hydrogen sensor 101, the resistance value of the first hydrogen sensor 101 decreases, and the voltage of the voltage output port 4 begins to decrease; when the air flows through the second hydrogen sensor 102, the resistance value of the second hydrogen sensor 102 decreases, and the voltage of the voltage output port 4 begins to increase and gradually stabilizes. At this time, the integrated structure of the ultrafast response hydrogen sensor recovers to the initial state, and the next hydrogen detection can be performed, wherein the response time is a time required for an initial resistance when there is no gas to be tested to change to 90% of the resistance after the gas to be tested is introduced.

According to calculation, the response time obtained by utilizing the first hydrogen sensor 101 in the Embodiment 1 alone is 7.76 seconds. The time required for the voltage differential signal to increase from the initial state to the peak is calculated as the response time obtained from the detection of the integrated structure of the ultrafast response hydrogen sensor proposed in this embodiment while the response time calculated in the Embodiment 1 is only 0.67 seconds, which greatly improves the hydrogen response speed.

Embodiment 2

The Embodiment 2 provides an integrated structure of an ultrafast response hydrogen sensor. The structure of the Embodiment 2 is different from that of the Embodiment 1 only in that the distance between the first hydrogen sensor 101 and the second hydrogen sensor 102 is adjusted to 15 cm. Other structures and materials in the Embodiment 2 are identical with the Embodiment 1.

Figure 4:
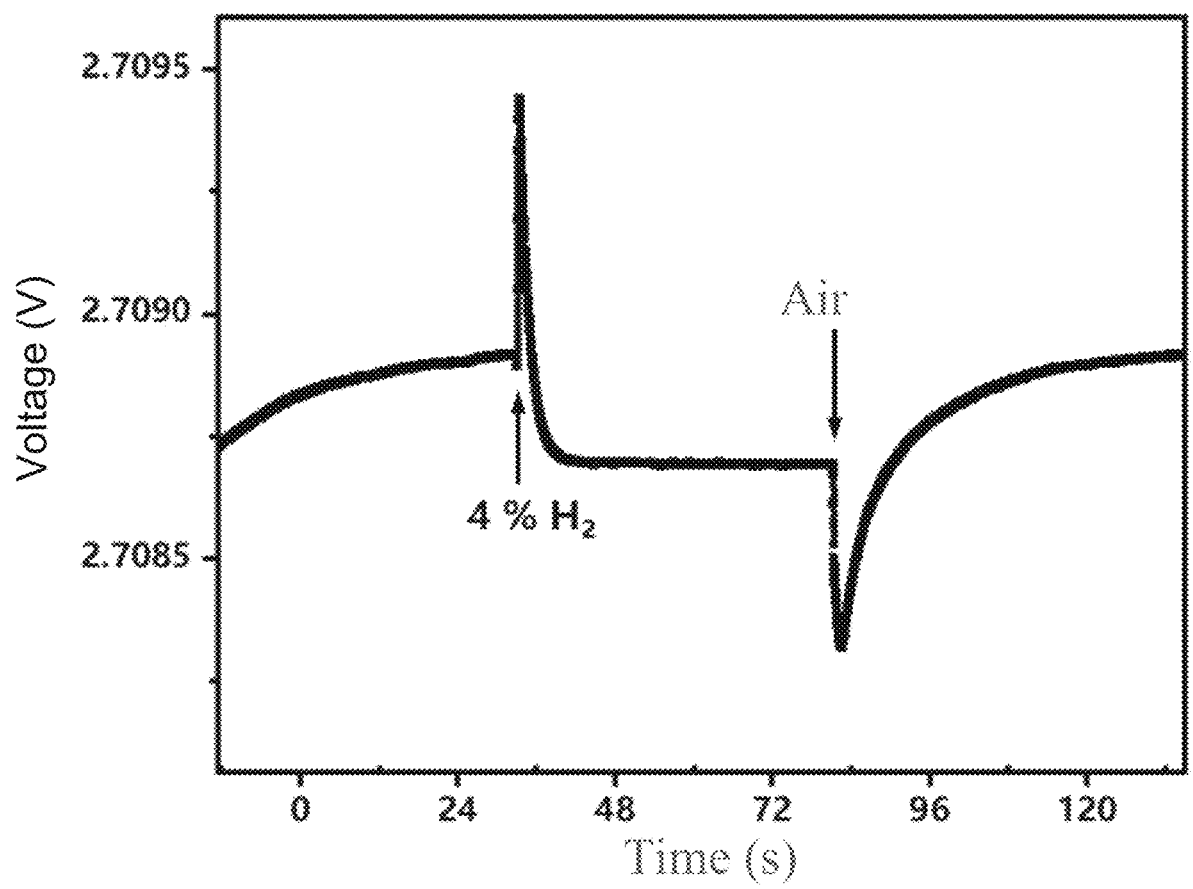
FIG. 4 is a hydrogen response voltage differential signal output curve outputted by the voltage output port according to an Embodiment 2 of the present invention.

Similarly, the performance test of the integrated structure of the ultrafast response hydrogen sensor provided in the Embodiment 2 is carried out. Specifically, the hydrogen with a concentration of 4% is detected, and the hydrogen response voltage differential signal output curve outputted by the voltage output port 4 as shown in FIG. 4 is obtained. The response time calculated is only 0.46 s, and a response rate is 0.53 times that of the Embodiment 1, which indicates that shortening the distance between the first hydrogen sensor 101 and the second hydrogen sensor 102 is helpful to improve the hydrogen response speed.

Embodiment 3

The Embodiment 3 provides an integrated structure of an ultrafast response hydrogen sensor. The structure of the Embodiment 3 is different from that of the Embodiment 1 only in that the distance between the first hydrogen sensor 101 and the second hydrogen sensor 102 is adjusted to 35 cm. Other structures and materials in the Embodiment 3 are identical with the Embodiment 1.

Figure 5:
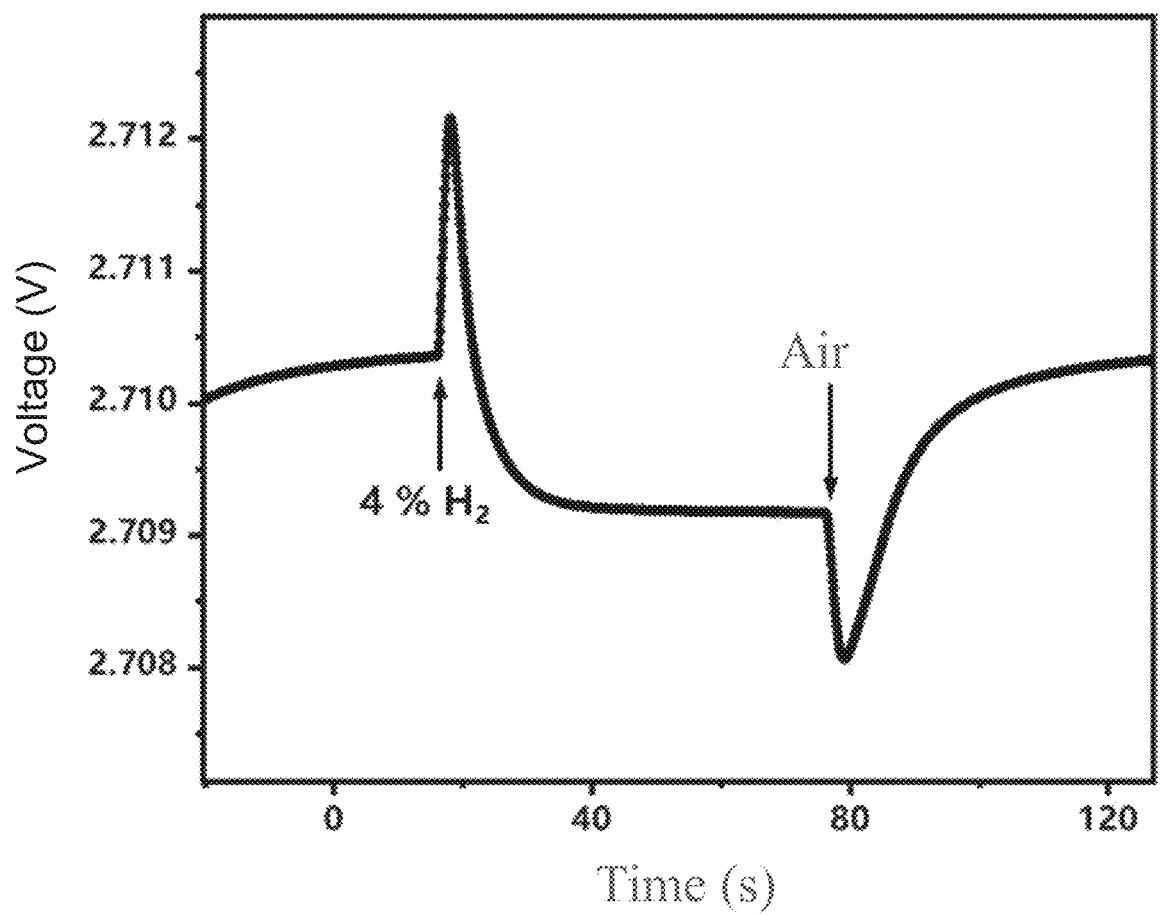
FIG. 5 is a hydrogen response voltage differential signal output curve outputted by the voltage output port according to an Embodiment 3 of the present invention.

Similarly, the performance test of the integrated structure of the ultrafast response hydrogen sensor provided in the Embodiment 3 is carried out. Specifically, the hydrogen with a concentration of 4% is detected, and the hydrogen response voltage differential signal output curve outputted by the voltage output port 4 as shown in FIG. 5 is obtained. The response time calculated is only 0.83 s, and a response rate is 1.63 times that of the Embodiment 3.

Embodiment 4

The Embodiment 4 provides an integrated structure of an ultrafast response hydrogen sensor. The structure of the Embodiment 4 is different from that of the Embodiment 1 only in that the gas flow rate generated by the gas extractor 3 is adjusted to 100 sccm. Other structures and materials in the Embodiment 4 are identical with the Embodiment 1.

Figure 6:
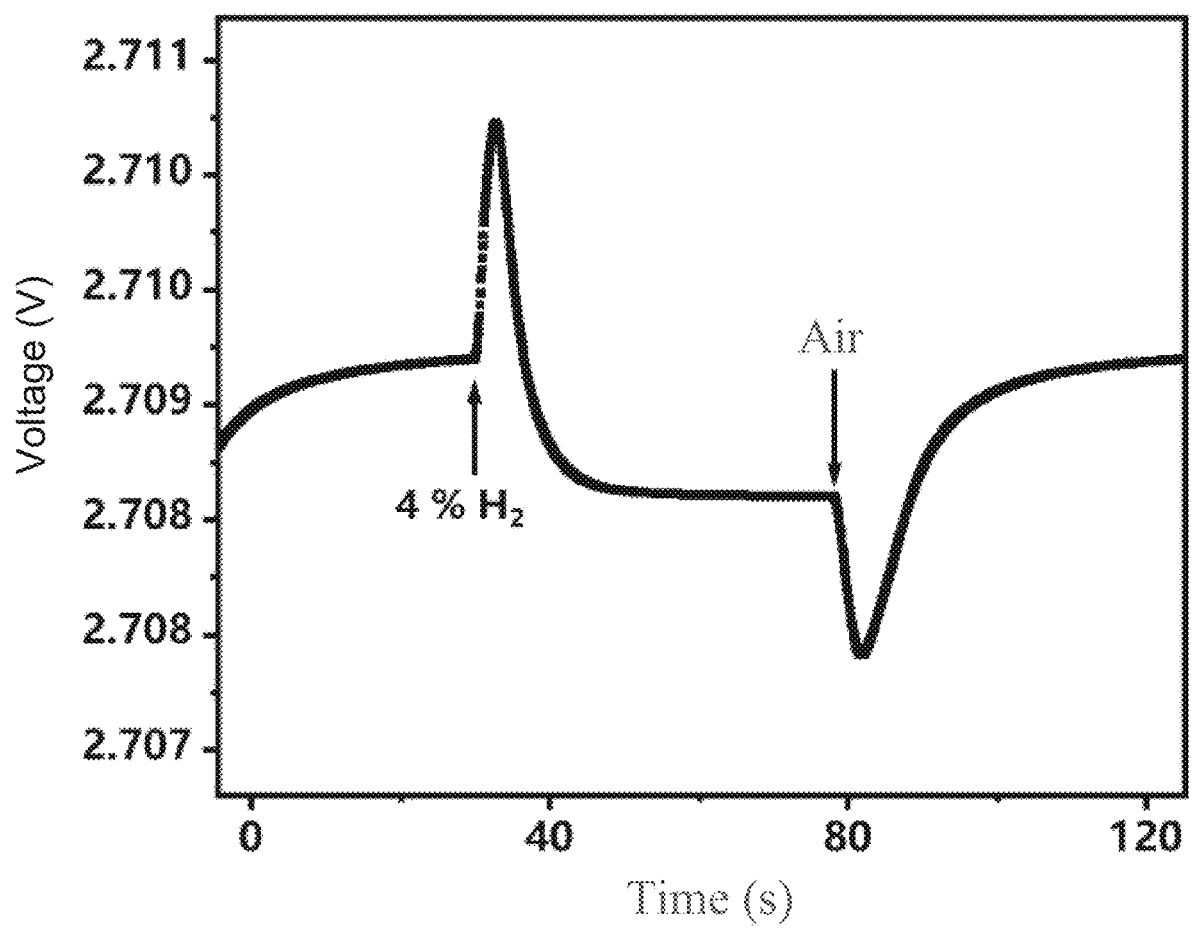
FIG. 6 is a hydrogen response voltage differential signal output curve outputted by the voltage output port according to an Embodiment 4 of the present invention.

Similarly, the performance test of the integrated structure of the ultrafast response hydrogen sensor provided in the Embodiment 2 is carried out. Specifically, the hydrogen with a concentration of 4% is detected, and the hydrogen response voltage differential signal output curve outputted by the voltage output port 4 as shown in FIG. 6 is obtained. The response time calculated is only 0.95 s, and a response rate is 1.45 times that of the Embodiment 1.

Embodiment 5

The Embodiment 5 provides an integrated structure of an ultrafast response hydrogen sensor. The structure of the Embodiment 5 is different from that of the Embodiment 1 only in that the gas flow rate generated by the gas extractor 3 is adjusted to 500 sccm. Other structures and materials in the Embodiment 5 are identical with the Embodiment 1.

Figure 7:
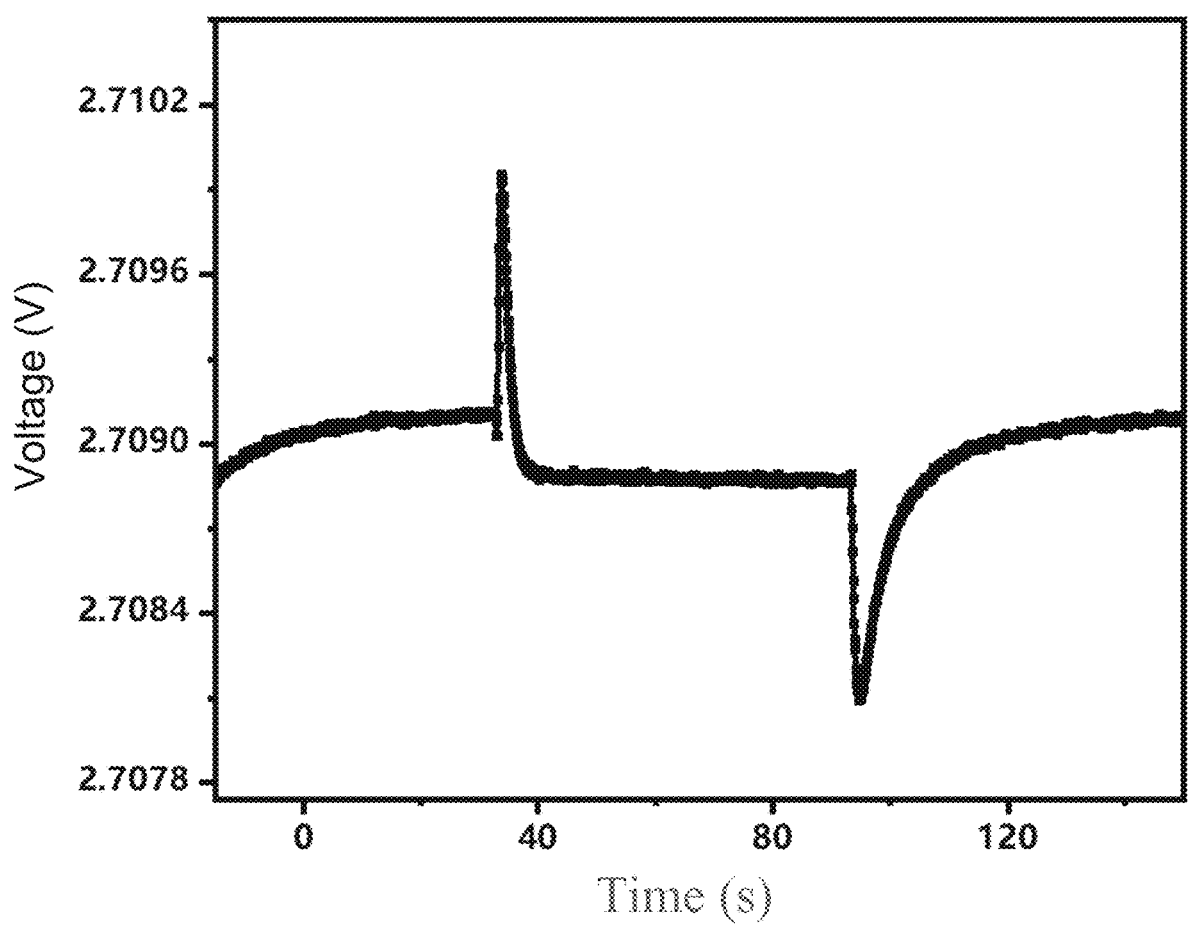
FIG. 7 is a hydrogen response voltage differential signal output curve outputted by the voltage output port according to an Embodiment 5 of the present invention.

Similarly, the performance test of the integrated structure of the ultrafast response hydrogen sensor provided in the Embodiment 2 is carried out. Specifically, the hydrogen with a concentration of 4% is detected, and the hydrogen response voltage differential signal output curve outputted by the voltage output port 4 as shown in FIG. 7 is obtained. The response time calculated is only 0.52 s, and a response rate is 0.74 times that of the Embodiment 1, which indicates that increasing the gas flow rate of the gas extractor is helpful to improve the hydrogen response rate.

In summary, the present invention utilizes the time difference between hydrogen reaching two hydrogen sensors and combines circuit design to collect the voltage differential signals of the two hydrogen sensors, thereby achieving rapid response of hydrogen and rapid detection of concentration; and by adjusting the distance between the two hydrogen sensors and the gas flow rate generated by the gas extractor, the hydrogen response time and response rate are controlled. The integrated structure of the ultrafast response hydrogen sensor of the present invention can be applied to scenarios with different hydrogen detection requirements.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:
1. A method of using an ultrafast response hydrogen sensor, wherein the ultrafast response hydrogen sensor comprises:
 a gas path chamber;

a gas mover fixed to a gas inlet of the gas path chamber; and a first hydrogen sensor and a second hydrogen sensor provided inside the gas path chamber;

wherein the first hydrogen sensor and the second hydrogen sensor have identical structure and hydrogen-sensitive characteristics;

wherein the gas mover is located in a straight line with the first hydrogen sensor and the second hydrogen sensor;

the first hydrogen sensor and the second hydrogen sensor each have an electrical connection A and an electrical connection B, and a DC voltage is applied to the electrical connection A of the first hydrogen sensor and the electrical connection B of the second hydrogen sensor, and the electrical connection B of the first hydrogen sensor is connected to the electrical connection A of the second hydrogen sensor to form a shared electrical connection, and the shared electrical connection serves as a voltage output;

wherein the method comprises:

flowing the hydrogen to the gas path chamber driven via the gas mover, flowing the hydrogen past the first hydrogen sensor and the second hydrogen sensor, converting a resistance differential signal between the first hydrogen sensor and the second hydrogen sensor into a voltage differential signal;

detecting the peak value of the voltage differential signal;

determining response time and response rate of the ultrafast response hydrogen sensor by detecting the time from the initial state to the peak of the voltage differential signal;

characterizing the hydrogen concentration based on the response time and the response rate;

after the hydrogen detection is completed, when the air flows the gas path chamber through the gas mover, restoring the ultrafast response hydrogen sensor to the initial state by flowing air through the gas mover and the gas path chamber.

2. The method as recited in claim 1, wherein a distance between the first hydrogen sensor and the second hydrogen sensor is in a range of 1 mm to 35 cm.

3. The method as recited in claim 1, wherein a gas flow rate generated by the gas extractor is in a range of 5-500 sccm.

4. The method as recited in claim 1, wherein a hydrogen-sensitive material of the first hydrogen sensor and the second hydrogen sensor is a palladium metal material, or a composite material consisting of a palladium metal material and at least one metal material, wherein the metal material is nickel, gold, ruthenium, cobalt or titanium.

5. The method as recited in claim 4, wherein the composite material is a layered material or an alloy material.

6. The method as recited in claim 1, wherein a distance between the first hydrogen sensor and the second hydrogen sensor, and a gas flow rate generated by the gas mover are adjusted to control the response time and the response rate of the ultrafast response hydrogen sensor.

* * * * *